US00PP19480P2

(12) United States Plant Patent

Sakazaki

(10) Patent No.: US PP19,480 P2

(45) Date of Patent: Nov. 25, 2008

(54) *CALIBRACHOA* PLANT NAMED 'USCALI402-1'

(50) Latin Name: ***Calibrachoa* sp.**
Varietal Denomination: USCALI402-1

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 11/978,126

(22) Filed: Oct. 25, 2007

(51) Int. Cl.
*A01H 5/00* (2006.01)

(52) U.S. Cl. ..... Plt./413

(58) Field of Classification Search ..... Plt./413
See application file for complete search history.

(56) References Cited

U.S. PATENT DOCUMENTS

PP11,558 P * 10/2000 Murakami ..... Plt./356
PP14,464 P2 * 1/2004 Pierce ..... Plt./413
PP15,387 P2 * 11/2004 Gass ..... Plt./226

OTHER PUBLICATIONS

UPOV ROM GTITM Computer Database, GTI Jouve Retrieval Software 20087/02 Citation for 'USCALI402–1'.*

* cited by examiner

*Primary Examiner*—Wendy C. Haas
(74) *Attorney, Agent, or Firm*—C. A. Whealy

(57) ABSTRACT

A new and distinct cultivar of *Calibrachoa* plant named 'USCALI402-1', characterized by its compact, mounding and outwardly spreading growth habit; numerous pale yellow-colored flowers; resistant to *Thielaviopsis;* and good garden performance.

1 Drawing Sheet

Botanical designation: *Calibrachoa* sp.
Cultivar denomination: 'USCALI402-1'.

BACKGROUND OF THE INVENTION

The present invention relates to a new and distinct cultivar of *Calibrachoa,* botanically known as *Calibrachoa* sp. and hereinafter referred to by the name 'USCALI402-1'.

The new *Calibrachoa* is a product of a planned breeding program conducted by the Inventor in Hikone, Shiga, Japan. The objective of the breeding program is to create new *Calibrachoa* cultivars with uniform plant habit and attractive flowers.

The new *Calibrachoa* originated from a cross-pollination made by the Inventor on Apr. 20, 2004 in Hikone, Shiga, Japan of a proprietary seedling selection of *Calibrachoa* sp. identified as code number CJ04-01, not patented, as the female, or seed, parent with a proprietary seedling selection of *Calibrachoa* sp. identified as code number CJ04-09, not patented, as the male, or pollen, parent. The new *Calibrachoa* was discovered and selected by the Inventor as a single flowering plant within the progeny of the stated cross-pollination in a controlled environment in Gensingen, Germany on May 24, 2005.

Asexual reproduction of the new *Calibrachoa* by terminal cuttings in a controlled environment in Gensingen, Germany since May 25, 2005 has shown that the unique features of this new *Calibrachoa* are stable and reproduced true to type in successive generations.

SUMMARY OF THE INVENTION

The cultivar USCALI402-1 has not been observed under all possible environmental conditions. The phenotype may vary somewhat with variations in environment and cultural practices such as temperatures, daylength and light intensity without, however, any variance in genotype.

The following traits have been repeatedly observed and are determined to be the unique characteristics of 'USCALI402-1'. These characteristics in combination distinguish 'USCALI402-1' as a new and distinct cultivar of *Calibrachoa:*

1. Compact, mounding and outwardly spreading growth habit.
2. Numerous pale yellow-colored flowers.
3. Resistant to *Thielaviopsis.*
4. Good garden performance.

The new *Calibrachoa* can be compared to plants of the female parent selection. Plants of the new *Calibrachoa* differ from plants of the female parent selection in the following characteristics:

1. Plants of the new *Calibrachoa* are not as upright as plants of the female parent selection.
2. Plants of the new *Calibrachoa* are more freely branching than plants of the female parent selection.

Plants of the new *Calibrachoa* can be compared to plants of the male parent selection. Plants of the new *Calibrachoa* differ from plants of the male parent selection in the following characteristics:

1. Plants of the new *Calibrachoa* are more upright than plants of the male parent selection.
2. Plants of the new *Calibrachoa* have larger flowers than plants of the male parent selection.

Plants of the new *Calibrachoa* can be compared to plants of the cultivar Sunbelki, disclosed in U.S. Plant Pat. No. 11,558. In side-by-side comparisons conducted in Gensingen, Germany, plants of the new *Calibrachoa* differed from plants of the cultivar Sunbelki in the following characteristics:

1. Plants of the new *Calibrachoa* flowered earlier than plants of the cultivar Sunbelki.
2. Plants of the new *Calibrachoa* and the cultivar Sunbelki differed in flower color as plants of the cultivar Sunbelki had yellow-colored flowers.

3. Plants of the new *Calibrachoa* were observed to be resistant to *Thielaviopsis* whereas plants of the cultivar Sunbelki were observed to susceptible to *Thielaviopsis*.

Plants of the new *Calibrachoa* can also be compared to plants of the cultivar KLECA05104, not patented. In side-by-side comparisons conducted in Gensingen, Germany, plants of the new *Calibrachoa* differed from plants of the cultivar KLECA05104 in the following characteristics:

1. Plants of the new *Calibrachoa* were more compact and upright than plants of the cultivar KLECA05104.
2. Plants of the new *Calibrachoa* were more freely branching than plants of the cultivar KLECA05104.
3. Plants of the new *Calibrachoa* and the cultivar KLECA05104 differed in flower color as plants of the cultivar KLECA05104 had lemon Yellow-colored flowers.

BRIEF DESCRIPTION OF THE PHOTOGRAPHS

The accompanying colored photographs illustrate the overall appearance of the new *Calibrachoa,* showing the colors as true as it is reasonably possible to obtain in colored reproductions of this type. Colors in the photographs may differ slightly from the color values cited in the detailed botanical description which accurately describe the colors of the new *Calibrachoa.*

The photograph at the bottom of the sheet comprises a side perspective view of a typical flowering plant of 'USCALI402-1' grown in a container.

The photograph at the top of the sheet comprises a close-up of typical flowers of 'USCALI402-1'.

DETAILED BOTANICAL DESCRIPTION

The aforementioned photographs and following observations, measurements a values describe plants grown in Bonsall, Calif., under commercial practice during the spring and summer in an outdoor nursery with day temperatures ranging from 7° C. to 35° C. and night temperatures ranging from 7° C. to 21° C. Rooted young plants were grown for about eight weeks in 15-cm containers. In the following description, color references are made to The Royal Horticultural Society Colour Chart, 1995 Edition, except where general terms of ordinary dictionary significance are used.

Botanical classification: *Calibrachoa* sp. cultivar USCALI402-1.

Parentage:

*Female, or seed, parent.*—Proprietary seedling selection of *Calibrachoa* sp. identified as code number CJ04-01, not patented.

*Male, or pollen, parent.*—Proprietary seedling selection of *Calibrachoa* sp. identified as code number CJ04-09, not patented.

Propagation:

*Type.*—By terminal cuttings.

*Time to produce a rooted young plant, summer.*—About three weeks at temperatures of 20° C.

*Time to produce a rooted young plant, winter.*—About four weeks at temperatures of 20° C.

*Root description.*—Fine; white in color.

*Rooting habit.*—Freely branching; dense.

Plant description:

*Plant and growth habit.*—Compact, mounding and outwardly spreading plant habit. Freely branching habit with about six to seven primary lateral branches each with multiple secondary lateral branches; pinching enhances branching. Moderately vigorous growth habit.

*Plant height.*—About 16 cm.

*Plant diameter.*—About 47.5 cm.

Lateral branch description:

*Length.*—About 29 cm.

*Diameter.*—About 2 mm.

*Internode length.*—About 1 cm.

*Strength.*—Strong.

*Aspect.*—Initially upright to outwardly spreading.

*Texture.*—Pubescent.

*Color.*—146C.

Foliage description:

*Arrangement.*—Before flowering, alternate, simple; after flowering, opposite, simple.

*Length.*—About 3.7 cm.

*Width.*—About 1.4 cm.

*Shape.*—Elliptical.

*Apex.*—Broadly acute.

*Base.*—Attenuate.

*Margin.*—Entire.

*Texture, upper and lower surfaces.*—Pubescent.

*Venation pattern.*—Pinnate; arcuate.

*Color.*—Developing foliage, upper surface: 146A. Developing foliage, lower surface: 146B. Fully expanded foliage, upper surface: 147A; venation, 147B. Fully expanded foliage, lower surface: 147B; venation, 147C.

*Petiole.*—Length: About 5 mm. Diameter: About 2 mm. Texture, upper and lower surfaces: Pubescent. Color, upper surface: 146B. Color, lower surface: 146D.

Flower description:

*Flower arrangement and habit.*—Single salverform flowers arranged singly arising from leaf axils. Freely flowering habit with usually about 27 open flowers and flower buds per lateral branch. Flowers persistent. Flowers face upright to mostly outwardly.

*Fragrance.*—None detected.

*Natural flowering season.*—Plants of the new *Calibrachoa* initiate and develop flowers about four to six weeks after planting. Plants flower continuously from April to October in Southern California.

*Flower longevity.*—Individual flowers last about five to seven days on the plant.

*Flower diameter.*—About 2.6 cm by 3 cm.

*Flower length (height).*—About 2.5 cm.

*Flower throat diameter.*—About 4 mm by 7 mm.

*Flower tube diameter, base.*—About 2 mm.

*Flower tube length.*—About 1.9 cm.

*Flower bud.*—Shape: Elongated oblong. Length: About 1.8 cm. Diameter: About 5 mm. Color: 4C.

*Corolla.*—Arrangement: Five petals fused at the base and opening into a flared trumpet. Petal length from throat: About 1.2 cm. Petal lobe width: About 1.5 cm. Petal shape: Roughly obovate. Petal apex: Rounded; slightly mucronate. Petal margin: Entire. Petal texture, upper surface: Smooth, velvety. Petal texture, lower surface: Pubescent. Throat texture: Smooth, velvety. Tube texture: Pubescent. Color: Petal, when opening, upper surface: 1C. Petal, when opening, lower surface: 1D. Petal, fully opened, upper surface: 1D; color towards the apex becoming closer to 4D with development; venation, 145A. Petal, fully opened, lower surface: 4D; venation, 145A. Throat: 154B; venation, 145B. Tube: 1C; venation, 145A.

*Calyx.*—Arrangement: One star-shaped calyx tube with five sepals fused at the base per flower. Sepal length: About 9 mm. Sepal width: About 2 mm. Sepal shape: Lanceolate. Sepal apex: Acute. Sepal margin: Entire. Sepal texture, upper and lower surfaces: Pubescent. Color, upper and lower surfaces: 144A.

*Peduncles.*—Length: About 1.8 cm. Diameter: About 1 mm. Angle: About 45° from stem axis. Strength: Moderately strong. Texture: Pubescent. Color: 145A.

*Reproductive organs.*—Stamens: Quantity/arrangement: About five per flower. Anther shape: Oval. Anther length: About 1 mm. Anther color: 5C. Pollen amount: Scarce. Pollen color: 1A. Pistils: Quantity: One per flower. Pistil length: About 1.1 cm. Style length: About 6 mm. Style color: 145C. Stigma shape: Oval. Stigma color: 145A. Ovary color: 145B.

*Seed/fruit.*—Seed and fruit development have not been observed on plants of the new *Calibrachoa.*

Garden performance: Plants of the new *Calibrachoa* have been observed to have good garden performance and tolerate wind, rain and temperatures ranging from about 1° C. to about 40° C.

Pathogen/pest resistance: Plants of the new *Calibrachoa* have been observed to be resistant to *Thielaviopsis.* Plants of the new *Calibrachoa* have not been observed to be resistant to pests and other pathogens common to *Calibrachoa.*

It is claimed:

1. A new and distinct *Calibrachoa* plant named 'USCALI402-1' as illustrated and described.

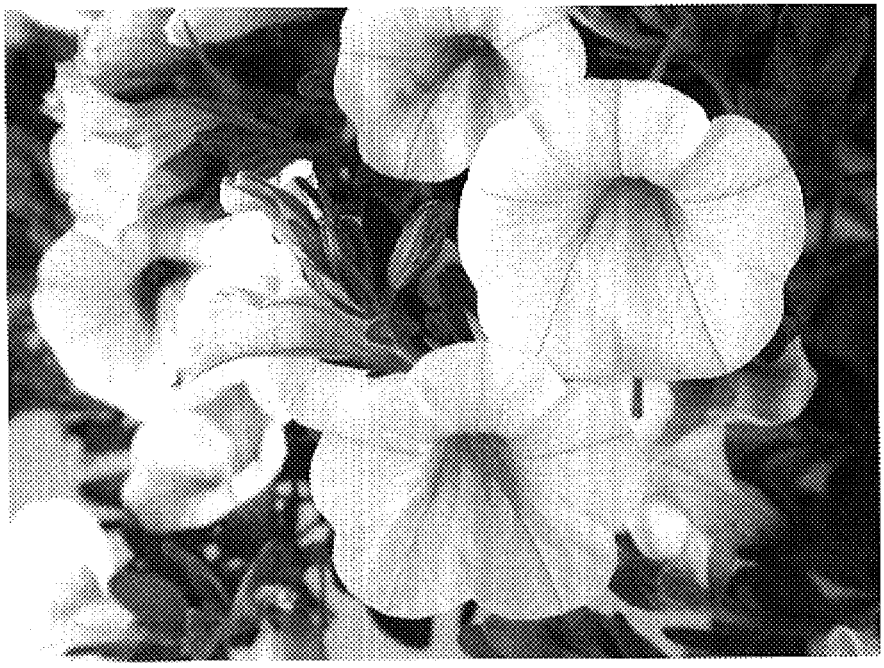
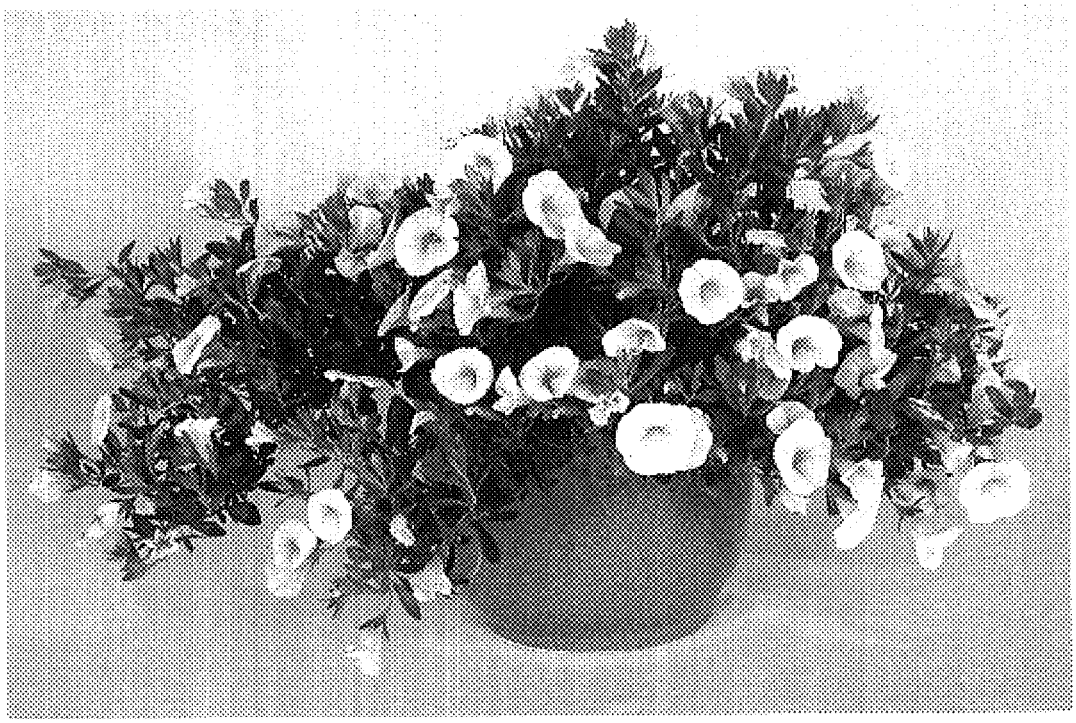

* * * * *